United States Patent [19]

Ohmura et al.

[11] Patent Number: 4,565,697
[45] Date of Patent: Jan. 21, 1986

[54] PROCESS FOR PRODUCING A HEPATITIS B INFECTION PREVENTING VACCINE

[75] Inventors: Takao Ohmura, Osaka; Terufumi Fujiwara; Akimasa Ohmizu, both of Hyogo, all of Japan; Satoshi Funakoshi, Los Angeles, Calif.

[73] Assignee: Green Cross Corporation, Osaka, Japan

[21] Appl. No.: 552,079

[22] Filed: Nov. 15, 1983

[30] Foreign Application Priority Data

Nov. 29, 1982 [JP] Japan ................................. 57-210240

[51] Int. Cl.$^4$ ..................... A61K 39/12; A61K 35/14; C12N 7/04; C12N 7/02
[52] U.S. Cl. ....................................... 424/89; 424/101; 435/236; 435/239
[58] Field of Search ................... 424/89, 101; 435/236, 435/239

[56] References Cited

U.S. PATENT DOCUMENTS

| | | | |
|---|---|---|---|
| 3,636,191 | 1/1972 | Blumberg et al. | 424/89 |
| 3,951,937 | 4/1976 | Vnek et al. | 424/89 X |
| 3,994,870 | 11/1976 | Neurath et al. | 260/112 R |
| 4,017,470 | 4/1977 | Izaka et al. | 260/112 B |
| 4,057,628 | 11/1977 | Bick | 424/101 |
| 4,162,192 | 7/1979 | Mizuno et al. | 424/89 X |
| 4,314,997 | 2/1982 | Shanbrom | 424/101 |
| 4,335,214 | 6/1982 | Adamowicz et al. | 435/239 |
| 4,404,187 | 9/1983 | Schwinn et al. | 424/101 |

FOREIGN PATENT DOCUMENTS

| | | | |
|---|---|---|---|
| 2611723 | 9/1977 | Fed. Rep. of Germany | 424/89 |
| 2488510 | 2/1982 | France | 424/89 |
| 0038617 | 4/1978 | Japan | 424/89 |
| WO81/00050 | 1/1981 | PCT Int'l Appl. | 424/89 |

OTHER PUBLICATIONS

Lehninger, A., *Biochemistry*, 2nd Ed., Worth Pub., N.Y., 1975, pp. 829-830.
Davis et al., *Microbiology*, 3rd Ed., Harper & Row, N.Y., 1980, pp. 1226-1227.

Primary Examiner—Sidney Marantz
Assistant Examiner—Shawn P. Foley
Attorney, Agent, or Firm—Berman, Aisenberg & Platt

[57] ABSTRACT

A process for producing a hepatitis B infection preventing vaccine containing hepatitis B surface antigen as a main component thereof which comprises removing human plasma components possibly causing adverse effects and components capable of causing hepatitis B infection by incorporating steps of fractionation using ammonium sulfate, adsorption on a colloidal silicate and fractionation using polyethylene glycol into the purification stage after heat treatment and further carrying out a treatment for infectivity inactivation without causing any antigenicity impairment.

2 Claims, No Drawings

PROCESS FOR PRODUCING A HEPATITIS B INFECTION PREVENTING VACCINE

This invention relates to a process for producing a hepatitis B infection preventing vaccine containing hepatitis B surface antigen (HBsAg) as main component thereof and, more particularly, to a process for producing such vaccine which comprises removing human plasma components possibly causing adverse effects and components capable of causing hepatitis B infection by incorporating steps of fractionation using ammonium sulfate, adsorption on a colloidal silicate and fractionation using polyethylene glycol into the purification stage after heat treatment and further carrying out a treatment for infectivity inactivation without causing any antigenicity impairment.

HBsAg is known to be a constituent of a virus capable of causing hepatitis B (HBV). However, most of it is present as minute particles lacking infectivity and it can be found in the human or chimpanzee plasma. Electrophoretically, HBsAg belongs to the class of human plasma globulin proteins.

According to one method of protection against HBV infection, an anti-HBs immunoglobulin preparation is administered so as to produce passive immunity, but the effect is of short duration. It goes without saying that active immunization with a vaccine is the most preferable, as can be seen in the prevention of usual viral infections.

Theoretically, a vaccine against hepatitis B would be provided by isolating a hepatitis B virus substance and inactivating the same by an appropriate method or by separating the unchanged virus from HBsAg followed by supplementary inactivation. This vaccine, when administered to man or animal, induces production of antibodies against the hepatitis B virus and as a result hepatitis B infection can be prevented.

Many attempts have so far been made to produce HBsAg vaccines. One method of viral infectivity inactivation consists in heat treatment at 60° C. for 10 hours or at 100° C. for 2 minutes. The heat treatment, however, cannot assure sufficient decomposition of nucleic acids (DNA) contained in HBV. Therefore, the technique now coming into wide use is the inactivation of HBV by treatment with formalin.

Meanwhile, even a slight amount of concomitant human plasma proteins, once modified by the formalin treatment in the course of vaccine production, may, on administration to man, cause adverse effects. Therefore, such proteins should be removed as completely as possible. This trace amount of accompanying human plasma components cannot be removed even by repeated runs of ultracentrifugation or affinity chromatography, so that some researchers took the view that part of such components should be present in the form bound to HBsAg.

The two most generally employed methods of isolating and purifying HBsAg are ultracentrifugation and affinity chromatography. By using these techniques, almost pure HBsAg particles can be obtained. However, the conventional methods of isolation are generally complicated and present difficulties in industrial utilization thereof.

Accordingly, an object of the present invention is to provide a commercial process (for producing a hepatitis B infection preventing vaccine containing HBsAg particles as main components thereof) which comprises removing plasma components, especially plasma proteins, possibly capable of causing adverse effects, while maintaining the antigenicity of HBsAg particles, then recovering HBsAg and further inactivating possibly accompanying HBV, that is Dane particles.

In carrying out the purifiaction of HBsAg, the present inventors combined the step of fractionation with ammonium sulfate, the step of adsorption on a colloidal silicate and the step of fractionation with polyethylene glycol and investigated intensively the conditions of treatment to be employed in each of these steps. As a result, they have now completed the present invention.

Thus, the present invention consists in a process for producing a hepatitis B infection preventing vaccine containing, as main components thereof, HBsAg free from human plasma components and incapable of causing hepatitis B infection, which comprises the steps of subjecting an aqueous solution of HBsAg-containing human plasma proteins to heat treatment at 50°–70° C. for 8–12 hours, removing from the so-treated aqueous solution those proteins precipitable by 10–20% saturation with ammonium sulfate, collecting those proteins precipitable by 40–50% saturation with ammonium sulfate, dissolving the same in water, bringing the aqueous solution into contact with a colloidal silicate, eluting HBsAg adsorbed on the colloidal silicate with a buffer containing 0.1–1.0% of a deoxycholic acid salt, pH 8.5–9.5, adjusting the thus-obtained eluate to neutrality or its vicinity, adding 3–7% (w/v) of polyethylene glycol and thereby removing HBV and immune complexes as a precipitate, adding to the supernatant polyethylene glycol to a concentration of 15–20% (w/v) and thereby collecting HBsAg as a precipitate, subjecting the precipitate to gel filtration using a gel filtration carrier equilibrated with a buffer having a pH 6–8 and applicable to high-molecular substances having a molecular weight of several hundred thousand to several million and thereby recovering an HBsAg fraction, recovering from said fraction a specific fraction of HBsAg particles having a particle size of 18–24 nm and a density of 1.18–1.22 g/cm$^3$, subjecting the fraction thus obtained to inactivation with formalin (formalin concentration: 1/1,500–1/2,500) at 35°–40° C. for 94–98 hours, allowing the fraction to stand at 2°–6° C. for 6–10 days, dialyzing the thus-inactivated HBsAg fraction against a buffer having a pH of 6–8, adding a vehicle and lyophilizing the resulting mixture.

The human plasma protein material to be used in the practice of the invention may be any HBsAg-containing one, for instance one capable of actually causing hepatitis in human or any other one in which antigenicity of HBsAg is detected. Thus, there may be used plasma, serum and various protein fractions obtainable by the known plasma protein fractionation techniques. Among the materials usable in the practice of the invention, $\alpha$- and $\beta$-globulin fractions, which are relatively rich in HBsAg distribution, are the most preferable. These fractions are also favorable as the starting materials because they are byproducts in the separation of other useful plasma proteins, there is used, for instance, plasma per se or a solution of the above-mentioned plasma protein materials in water (e.g. distilled water).

Using such HBsAg-containing human plasma protein material as the starting material, a hepatitis B infection preventing vaccine is produced via the following steps:

(1) Step of heat treatment (50°–70° C., 8–12 hours):

In the starting aqueous human plasma protein solution containing HBsAg, there is optionally dissolved sodium azide, preferably in an amount of 0.1–0.3 g per liter of said aqueous solution. After dissolution of the sodium azide, the solution is subjected to heat treatment at 50°–70° C. for 8–12 hours, which leads to loss of hepatitis B infectivity but not to loss of antigenicity. This step may also be conducted optionally with a known stabilizer added.

(2) Step of fraction with ammonium sulfate (10–20% saturation):

The aqueous solution after the above heat treatment step is subjected to fractionation by 10–20% saturation with ammonium sulfate, whereby those proteins precipitable by such ammonium sulfate saturation are removed. Said fractionation is effected, for example, by adjusting the pH of the heat-treated above aqueous solution to 4–6 (preferably with hydrochloric acid or sulfuric acid, for instance), adding ammonium sulfate to a saturation degree of 10–20% and stirring the mixture at 3°–5° C. for 30–120 minutes. The resulting protein precipitate is removed, after allowing to stand for 30–120 minutes, for instance, by centrifugation (generally at 6,000–8,000 r.p.m. for 10–30 minutes) and the supernatant is recovered.

(3) Step of fractionation with ammonium sulfate (40–50% saturation):

The proteins precipitable by 40–50% saturation with ammonium sulfate are recovered from the above centrifugation supernatant. Said fractionation is generally conducted at pH 6–8. For the pH adjustment, an alkali metal hydroxide (e.g. sodium hydroxide) is generally used. The fractionation is preferably carried out at a temperature of 3°–5° C. and preferably with stirring for 30–120 minutes. Standing, for example, for 30–120 minutes after such stirring results in formation of a precipitate. This precipitate is preferably recovered by centrifugation (generally at 6,000–8,000 r.p.m. for 10–30 minutes).

(4) Step of adsorption treatment with a colloidal silicate:

As the colloidal silicate, there may be used silica gel, magnesium aluminosilicate, diatomaceous earth, acid clay or kaolin. Said step is conducted, for instance, in the following manner:

First, the protein precipitate obtained in the above ammonium sulfate fractionation step is dissolved in a buffer having a pH of 6–8 (e.g. phosphate buffer), if necessary followed by dialysis, clarification and/or sterilization by filtration. Thereafter, a colloidal silicate is added, preferably to a concentration of 1–4% (w/v), and the mixture is stirred, preferably at a temperature of 36°–38° C. for 2–4 hours.

The colloidal silicate with HBsAg adsorbed thereon is recovered, for example by centrifugation (generally at 2,000–4,000 r.p.m. for 10–20 minutes). Preferably, the so-recovered colloidal silicate is washed, for example, with a buffer having a pH of 7–8 (e.g. buffer with pH 7–8 containing a chelating agent, such as 0.1–0.2 M ethylene-diaminetetraacetic acid, and/or an inorganic salt, such as 0.1–0.2 M sodium chloride).

(5) Step of elution with a deoxycholate-containing buffer (pH 8.5–9.5):

In this step, the HBsAg adsorbed in the preceding step is eluted. As the deoxycholate, there is used an alkali metal salt (e.g. sodium salt), among others. In a typical embodiment of this step, the adsorption product obtained in the preceding step is subjected to elution with a buffer having a pH of 8.5–9.5 and containing 0.1–1% of a deoxycholate. Then, the HBsAg-containing eluate is recovered by centrifugation (e.g. at 2,000–4,000 r.p.m. for 10–20 minutes).

(6) Step of fractionation with polyethylene glycol: (i) Step of fractionation with polyethylene glycol (3–7% (w/v)):

In the crude HBsAg obtained in the step of adsorption treatment with colloidal silicate, trace contaminants, such as HBV and immune complexes, are removed as a precipitate by fractionation with polyethylene glycol (generally having a molecular weight of 2,000–10,000). This step of fractionation with polyethylene glycol is performed by adding polyethylene glycol to the eluate from the colloidal silicate with HBsAg adsorbed thereon to a polyethylene glycol concentration of 3–7% (w/v), followed by stirring at 2°–10° C. for 10–60 minutes, with the pH being around neutrality (6–8). Thereafter, the mixture is allowed to stand for 3–7 hours. The resulting precipitate is removed as contaminant by centrifugation (e.g. at 1,000–5,000 r.p.m. for 20–40 minutes) and the supernatant is recovered.

(ii) Step of fractionation with polyethylene glycol (15–20% (w/v)):

Polyethylene glycol (generally having a molecular weight of 2,000–10,000) is added to the thus-obtained supernatant to a concentration of 15–20% (w/v) under the same conditions as above and the resulting precipitate is recovered. Generally, following the addition of polyethylene glycol, stirring is conducted at a temperature of 2°–10° C. for 10–60 minutes and then the mixture is allowed to stand for 16–20 hours. The resulting HBsAg-containing protein precipitate is recovered by centrifugation (e.g. at 8,000–12,000 r.p.m. for 40–50 minutes). The so-recovered protein precipitate is dissolved in a buffer, such as phosphate buffer with pH 6–8.

(7) Step of gel filtration:

In the gel filtration, molecular sieve carriers applicable to substances having molecular weights between several hundred thousand and several million, such as agarose (Sepharose 4B, 6B), crosslinked dextran and other high molecular polysaccharide granules, are employed.

The aqueous solution of the HBsAg-containing protein precipitate obtained from the step of fractionation with polyethylene glycol is applied to a molecular sieve carrier, followed by elution with a buffer, such as phosphate buffer with pH 6–8. An HBsAg fraction is thus recovered. The recovery of the HBsAg fraction is carried out while assaying the HBsAg-positive fractions by an immunological method.

(8) Step of ultracentrifugation:

In this step of ultracentrifugation, the zonal centrifugation in a linear cesium chloride density gradient (1.05–1.35 g/cm$^3$) is preferred. A typical mode of practice is as follows:

First, a density gradient is constructed in a 1,700-ml zonal rotor using cesium chloride solutions differing in density from 1.05 to 1.35 g/cm$^3$. Thereafter, the HBsAg fraction obtained in the preceding gel filtration step is poured into the rotor, then 50–100 ml of the buffer used in the preceding gel filtration step, such as phosphate buffer with pH 6–8, is poured thereinto, and ultracentrifugation is conducted at 30,000–34,000 r.p.m. for 35–40 hours.

Those HBsAg particles having a size of 18–24 nm, especially about 22 nm, are recovered from the density range of 1.18–1.22 g/cm$^3$.

(9) Step of inactivation with formalin:

If necessary, the thus-purified HBsAg fraction is adjusted to a concentration of 300-500 μg/ml. Then, formalin is added to a final concentration of 1/1,500-1/2,500. The mixture is kept, for example, at 35°-40° C. for 94-98 hours and further allowed to stand at 2°-10° C. for 6-10 days.

The thus-obtained inactivated HBsAg solution is dialyzed against a buffer, such as 0.01-0.05 M phosphate buffer with pH 6-8, preferably for 30 hours or longer. After dialysis, sterilization by filtration is performed as necessary, the dialysate is adjusted to a concentration of 60-100 μg/ml with a similar buffer, and about 1-5% (w/v) of a known vehicle known in the art, such as mannitol, lactose or glycine, is added. Thereafter, the resulting mixture is distributed among containers and lyophilized to give a hepatitis B infection preventing vaccine preparation.

The vaccine in accordance with the present invention is preferably used in the state adsorbed on an immunological adjuvant so as to increase its immunizing potency. As such adjuvant, there may be used aluminum hydroxide or aluminum sulfate, for instance.

When lyophilization is carried out after addition of an immunological adjuvant, such as aluminum hydroxide, changes are observed on the aluminum hydroxide particles. Therefore, in using the vaccine according to the invention in the state adsorbed on an immunological adjuvant, it is preferable to dissolve the lyophilisate in a diluent (e.g. 1.6% sodium chloride solution), then add an aqueous suspension of the immunological adjuvant (e.g. aluminum hydroxide suspension) so as to cause adsorption of HBsAg thereon, and administer the suspension as an injection.

It is therefore preferable to provide the vaccine in accordance with the invention in the form of a kit comprising the lyophilized vaccine, a diluent and an immunological adjuvant.

After addition of an aluminum hydroxide suspension, 98% or more of HBsAg is adsorbed on aluminum hydroxide within 20 seconds.

The vaccine according to the invention is administered parenterally, for instance intramuscularly or subcutaneously (preferably subcutaneously).

The vaccine according to the invention is free of hepatitis B infectivity and of human plasma components and therefore can be used very safely. Furthermore, since it is a lyophilisate, it has particular advantages such as:

(1) that it can be stored for a long period;

(2) that it does not contain thimerosal (Mercury antiseptic);

(3) that since it is free of suspended aluminum hydroxide, insoluble foreign matters formed by precipitation during storage can easily be detected;

(4) that it can be used in varied concentrations; and (5) that the HBsAg titer can easily be measured (possibility of checking deactivation).

Test Example

For confirming the safety of the vaccine according to the invention, the product of Example 1 was administered to the chimpanzee known to be the only animal species other than the human that could be infected with HBsAg. Two chimpanzees were given a dose of 20 μg (a single dose for adult humans) and other two were given 2 mg (100 times the single dose for adult humans). In each case, the vaccine was administered intravenously. During the 7-month observation period following the administration the 4 chimpanzees were normal in liver function test, hematological test, liver biopsy and HBsAg test. In particular, no appearance of HBc antibody was observed. The safety has thus been proved.

Then, a Phase I clinical study was conducted by administering the vaccine to a small number of healthy volunteers. As a result, no abnormalities were found in various tests for safety confirmation (adverse reaction, liver function test, hematological test) or any appearance of HBc antibody was not observed. The safety of this vaccine in humans has thus verified. In all the volunteers given the vaccine, production of HBs antibody was noted, suggesting the effectiveness of this vaccine in the prevention of HBsAg infection.

The following examples are illustrative but never limitative of the present invention. In the examples, HBsAg was tested by the reversed passive hemagglutination method (RPHA method, Japanese Tokkyo Kokai Koho No. 50-12,227) using Antihebscell (product of the Green Cross Co.).

EXAMPLE 1

Fifty liters of pooled plasma with an HBsAg titer of 1:4,000 by the RPHA method were heated at 60° C. for 10 hours, and then adjusted to pH 5 with 1 N hydrochloric acid. Ammonium sulfate was added thereto to 15% saturation, and the mixture was stirred at 4° C. for 60 minutes, followed by standing for 60 minutes. The resultant precipitate was removed by centrifugation (7,000 r.p.m., 20 minutes). The supernatant was adjusted to pH 7 with 1 N sodium hydroxide, then ammonium sulfate was added to 45% saturation, and the mixture was stirred at 4° C. for 60 minutes. After allowing to stand for 60 minutes, the resultant precipitate was recovered by centrifugation (7,000 r.p.m., 20 minutes). The precipitate proteins recovered were dissolved in phosphate buffer, pH 7, then magnesium aluminosilicate (Aerosil R380, Degusa) was added to a concentration of 2.5% (w/v), and the mixture was stirred at 37° C. for 3 hours. Thereafter, the magnesium aluminosilicate with HBsAg adsorbed thereon was recovered by centrifugation (3,000 r.p.m., 15 minutes). The so-recovered magnesium aluminosilicate with HBsAg adsorbed thereon was washed with a buffer (pH 7.5) containing 0.15 M ethylenediaminetetraacetic acid and 0.15 M sodium chloride. Thereafter, the HBsAg adsorbed was eluted with a buffer (pH 9.0) containing 0.5% of sodium deoxycholate, followed by centrifugation (3,000 r.p.m., 15 minutes). The thus-recovered HBsAg-containing eluate was adjusted to pH 7 with 1 N hydrochloric acid, then polyethylene glycol (molecular weight 6,000) was added to a concentration of 4% (w/v), and the mixture was stirred at 4° C. for 30 minutes. After standing for 5 hours, the mixture was centrifuged (3,000 r.p.m., 30 minutes) and the supernatant was recovered. To the supernatant obtained, there was added polyethylene glycol 4,000 to a concentration of 20% (w/v). The mixture was stirred at 4° C. for 30 minutes and then allowed to stand for 18 hours. The resultant protein precipitate was recovered by centrifugation (10,000 r.p.m., 45 minutes). The so-recovered protein precipitate was dissolved in phosphate buffer, pH 7. This HBsAg-containing aqueous solution of precipitated proteins was subjected to gel filtration with phosphate buffer, pH7 using Sepharose 4B as the molecular sieve carrier. HBsAg fraction was pooled. From the HBsAg fraction obtained by gel filtration, an HBsAg fraction in the density region of 1.18–1.22 g/cm³ was recovered by zonal centrifugation (32,000 r.p.m., 37 hours) in a linear cesium chloride density gradient (1.05–1.35 g/cm³). The HBsAg fraction thus recovered was adjusted to a concentration of 400 μg/ml with phosphate buffer (pH 7), then kept at 37° C. for 96 hours with formalin added in a concentration of 1/2,000, and allowed to stand at 4° C. for 8 days. Thereafter, the fraction was dialyzed against 0.02 M phosphate buffer (pH 7) so as to remove the remaining portion of formalin. There was obtained a solution of inactivated HBsAg.

EXAMPLE 2

The solution of inactivated HBsAg as obtained in Example 1 was adjusted to a concentration of 80 μg/ml, then 2% (w/v) of mannitol was added, and the mixture was sterilized by filtration, dispensed among 10-ml vials in 2.5-ml portions and lyophilized to give a hepatitis B infection preventing vaccine.

The diluent and immunological adjuvant to be annexed to the lyophilized hepatitis B infection preventing vaccine obtained above were prepared in the following manner. The diluent was prepared by dispensing 1.6% sodium chloride solution in 2.5-ml portions into ampules and subjected to autoclave sterilization. The immunological adjuvant was prepared by adjusting the concentration of Alu Gel S 2% suspension (SERVA, West Germany) to 0.1% with distilled water for injection, dispensed in 2.5-ml portions into ampules and subjected to autoclave sterilization.

What is claimed is:

1. A process for producing a hepatitis B infection preventing vaccine containing, as main component thereof, hepatitis B surface antigen (HBsAg) and free of hepatitis B infectivity and of human plasma components which comprises the steps of:
    (a) subjecting an aqueous solution of a human plasma protein fraction containing hepatitis B surface antigen to heat treatment at 50°–70° C. for 8–12 hours,
    (b) removing from the so-treated aqueous solution those proteins precipitate by 10–20% saturation with ammonium sulfate by such ammonium sulfate saturation,
    (c) collecting those proteins precipitable by 40–50% saturation with ammonium sulfate by such ammonium sulfate saturation,
    (d) bringing an aqueous solution of the proteins precipitated in (c) into contact with a colloidal silicate and thereby causing HBsAg to be adsorbed on said colloidal silicate,
    (e) eluting that portion of HBsAg adsorbed with a buffer (ph 8.5 to 9.5) containing 0.1–1% of a deoxycholic acid salt,
    (f) adjusting the elute thus-obtained substantially to neutrality,
    (g) adding polyethylene glycol to a level of 3–7% (w/v) and thereby removing hepatitis B virus (HBV) and immune complexes as a precipitate from supernatant,
    (h) increasing the polyethylene glycol concentration in the supernatant to 15–20% (w/v), thus collecting HBsAg as a precipitate,
    (i) subjecting the precipitate from (h) to gel filtration using a gel filtrating carrier equilibrated with a buffer having a pH of 6–8 and applicable to substances having a molecular weight of several hundred thousand to several million and thereby removing an HBsAg fraction,
    (j) recovering a specific HBsAg fraction having a particle size of 18–24 nm and a density of 1.18–1.22 g/cm³ by ultracentrifugation,
    (k) inactivating the fraction from (j) at a formalin concentration of 1/1,500–1/2,500 at 35°–40° C. for 94–98 hours,
    (l) allowing the resulting product to stand at 2°–6° C. for 6–10 days,
    (m) dialyzing the inactivated HBsAg fraction from (l) against a buffer with pH 6–8,
    (n) adding a vehicle and lyophilizing the resulting mixture.

2. A process for producing a hepatitis B infection preventing vaccine, which is free from hepatitis B infectivity and free from human plasma components, which comprises:
    (a) subjecting an aqueous solution of a human plasma protein fraction containing hepatitis B surface antigen to heat treatment at from 50° to 70° C. for from 8 to 12 hours,
    (b) admixing sufficient ammonium sulfate with the thus-treated aqueous solution to obtain from 10 to 20% ammonium sulfate saturation and removing thus-precipitated protein from the resulting supernatant,
    (c) admixing sufficient ammonium sulfate with supernatant from (b) to prepare from 40 to 50% ammonium sulfate saturation in said supernatant and collecting thus-precipitated proteins,
    (d) preparing an aqueous solution of the proteins precipitated in (c) and contacting same with colloidal silicate to adsorb HBsAg on the colloidal silicate,
    (e) eluting thus-adsorbed HBsAg from the colloidal silicate with a buffer (pH 8.5 to 9.5) containing from 0.1 to 1% of a deoxycholic acid salt,
    (f) neutralizing or substantially neutralizing the eluate from (e),
    (g) admixing from 3 to 7% (w/v) of polyethylene glycol (PEG) having a molecular weight of from 2,000 to 10,000 with eluate from (f) to precipitate hepatitis B virus (HBV) and immune complexes, and removing the resulting precipitate from supernatant,
    (h) adding sufficient PEG to the supernatant from (g) to obtain a PEG concentration of from 15 to 20% (w/v) and to precipitate HBsAg,
    (i) subjecting resulting precipitate to gel filtration, with a gel filtration carrier equilibrated with buffer having a pH of from 6 to 8 and applicable to substances having a molecular weight of from several hundred thousand to several million, and thus recovering an HBsAg fraction,
    (j) ultracentrifuging the HBsAg fraction to recover a specific HBsAg fraction having a particle size of from 18 to 24 nm and a density of from 1.18 to 1.22 g/cm³,
    (k) inactivating the fraction recovered from (j) by subjecting it to a formalin concentration of from 1/1,500 to 1/2,500 at from 35° to 40° C. for from 94 to 98 hours,
    (l) maintaining the product from (k) at from 2° to 6° C. for from 6 to 10 days,
    (m) dialyzing the product from (l) against a buffer with pH from 6 to 8, and
    (n) lyophilizing the resulting mixture.

* * * * *